United States Patent [19]
Craig, Jr.

[11] Patent Number: 5,162,574
[45] Date of Patent: Nov. 10, 1992

[54] BIS(4-CYANATOPHENYL)-1,1-ETHANE

[75] Inventor: Wallace M. Craig, Jr., Louisville, Ky.

[73] Assignee: Hi-Tek Polymers, Inc., Jeffersontwon, Ky.

[21] Appl. No.: 581,778

[22] Filed: Sep. 13, 1990

Related U.S. Application Data

[60] Division of Ser. No. 340,526, Apr. 19, 1989, abandoned, which is a continuation-in-part of Ser. No. 210,175, Jun. 20, 1988, Pat. No. 4,839,442, which is a continuation of Ser. No. 934,189, Nov. 24, 1986, abandoned.

[51] Int. Cl.⁵ .......................................... C07C 261/00
[52] U.S. Cl. .................................................. 560/301
[58] Field of Search .............................. 560/301; 558/9

[56] References Cited

U.S. PATENT DOCUMENTS

| | | | |
|---|---|---|---|
| 3,107,261 | 10/1963 | Gerber et al. | 560/301 |
| 3,448,079 | 6/1969 | Grigat et al. | 260/59 |
| 3,553,244 | 1/1971 | Grigat et al. | 260/453 |
| 3,740,348 | 6/1973 | Grigat et al. | 260/453 |
| 3,755,402 | 2/1973 | Grigat et al. | 260/453 |
| 3,994,949 | 11/1976 | Meyer et al. | 260/453 |
| 4,026,913 | 5/1977 | Tanigaichi et al. | 260/453 |
| 4,028,393 | 6/1977 | Rottloff et al. | 260/453 |
| 4,046,796 | 9/1977 | Rottloff et al. | 260/453 |
| 4,060,541 | 11/1977 | Sundermann | 260/453 |
| 4,709,008 | 11/1987 | Shimp | 528/422 |
| 4,748,270 | 5/1988 | Murray et al. | 560/301 |
| 4,831,086 | 5/1989 | Des et al. | 528/142 |
| 4,839,442 | 6/1989 | Craig, Jr. | 560/301 |
| 4,940,848 | 7/1990 | Shimp | 156/307.4 |
| 4,981,994 | 1/1991 | Jackson | 560/301 |

Primary Examiner—Mary C. Lee
Assistant Examiner—Robert C. Whittenbaugh
Attorney, Agent, or Firm—Herbert P. Price

[57] ABSTRACT

Bis(4-cyanatophenyl)-1,1-ethane, a low viscosity liquid, is useful in wet filament winding, resin transfer molding and pultrusion processes.

7 Claims, No Drawings

BIS(4-CYANATOPHENYL)-1,1-ETHANE

CROSS REFERENCE

This application is a division of Ser. No. 07/340,526, filed Apr. 19, 1989 now abandoned which is a continuation-in-part of Ser. No. 07/210,175, filed June 20, 1988, (now U.S. Pat. No. 4,839,442) which is a continuation of Ser. No. 06/934,189, filed Nov. 24, 1986 (now abandoned).

BACKGROUND OF THE INVENTION

The field of art to which this invention pertains is aryl cyanate esters, i.e., cyanic acid esters of polyhydric phenols.

Industry is constantly searching for lighter, stronger and more resistant materials to be used in place of the materials used today. For example, the aerospace industry is devoting considerable effort to utilizing structural composites in place of metals. Structural composites based on thermoplastic or thermoset resins and glass or carbon fibers have been and are being used successfully in many parts of military and commercial aircraft. Thermoset resins which are being used in such applications are epoxy resins, bismaleimide resins, and cyanate ester resins.

Cyanate ester resins, which are finding increasing use in structural composites, adhesives and electrical grade insulation are based on the reaction products of polyhydric phenols and cyanogen halides. Such resins and their methods of preparation are described in U.S. Pat. Nos. 3,403,128 and 3,755,042. Additional patents which describe cyanate esters are U.S 3,987,230 and 4,330,658.

Commercially available cyanate esters are either crystalline solids having melting points above 70° C. or are amorphous semisolids having viscosities at 25° C. of more than 100,000 cps. Such cyanate ester resins are difficult to use in many commercial operations. Manufacturers continue to employ them in many processes because of their superior physical and electrical properties when cured. Such resins, however, are not suitable for fabrication of structural composites using wet filament winding, resin transfer molding and pultrusion processes. These newer processes are more economical than the labor intensive procedure of hand placing tacky, drapable prepregs onto a mold followed by vacuum bag construction and autoclave curing.

Wet filament winding, resin transfer molding and pultrusion all require rapid on-line wetting and impregnation of continuous fiber reinforcement. Such a procedure requires resin viscosities in the range of 100 to 10,000 cps together with a catalyzed pot-life of 2 to 24 hours and gelation within 0.5 to 10 minutes at temperatures of 150°–180° C. In order to obtain a suitable viscosity, crystalline and semisolid amorphous cyanate esters must be heated to elevated temperatures, which requires a compromise between the catalyzed pot-life requirement and the rapid gelation requirement.

Resin transfer molding processes are operable using resins having viscosities of less than 2000 cps with the preferred range being 100–200 cps. Pultrusion operations can be conducted with resins having viscosities at 400 to 5,000 cps with the preferred range being 400 to 1100 cps. The viscosity requirements for resins used in filament winding processes are 500 to 10,000 cps with the preferred range being 500 to 1500 cps.

There is a need then for cyanate ester resins which have low viscosities, long term stability and fast curing capabilities when properly catalyzed.

SUMMARY OF INVENTION

This invention is directed to a specific cyanate ester, namely bis(4-cyanatophenyl)-1,1-ethane. In one aspect, this invention pertains to bis(4-cyanatophenyl)-1,1-ethane having a low viscosity and long term stability. In another aspect, this invention relates to a process for preparing bis(4-cyanatophenyl)-1,1-ethane having a low level of impurities.

The composition of matter of this invention is bis(4-cyanatophenyl)-1,1-ethane which is a polycyanate ester represented by the structure:

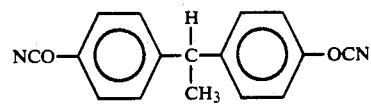

This polycyanate ester has a viscosity of less than 200 cps at 25° C., a reactivity at 110° C. of less than 0.3 percent trimerization per hour, and contains impurities of less than 50 ppm of tertiary amine and less than 1000 ppm of dialkylcyanamide.

The composition of this invention is made by reacting cyanogen chloride in a halocarbon solvent with a halocarbon solution of bis(4-hydroxyphenyl)-1,1-ethane and a tertiary amine at a temperature below −10° C. for a time sufficient to complete the esterification reaction followed by washing with acidified water wherein a small excess, based on equivalent weight, of cyanogen chloride is reacted with the dihydric phenol, and the amount of tertiary amine is in slight equivalent excess over the dihydric phenol.

When properly cured, the composition of this invention produces thermoset plastics which have superior hot-wet mechanical properties (heat deflection temperature, flexure strength and flexural modulus) and low moisture absorption properties.

The composition of this invention finds uses in the formulation of tacky/drapable prepregs for structural composite end use, as tacky/compliant structural film adhesives, transfer molding resins, filament winding resins, pultrusion resins, high solids coatings, and electrical insulating (impregnating) varnishes, die-attach adhesives and reaction injection molding compounds.

DESCRIPTION OF THE INVENTION

The aromatic cyanate ester group is a reactive group which when properly catalyzed readily reacts with other cyanate ester groups. This reactivity is important to the thermosetting character of polycyanate esters. However, this reactivity is also detrimental to the shelf-life and storage stability of the esters. Impurities in the cyanate ester, particularly residual tertiary amines used in the ester's manufacture, can catalyze the trimerization of the cyanate ester groups causing increases in viscosity and eventual gelation of the ester. Traces of hydroxyl groups from unreacted phenol enhance the catalytic effect of the tertiary amines which results in even shorter shelf life.

Another detrimental impurity that can be present in the cyanate ester product is dialkylcyanamide which results from the reaction of cyanogen chloride with a tertiary amine:

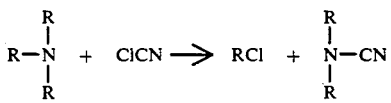

Dialkylcyanamide is a weak base and has very little effect upon the storage stability of the cyanate ester. However, the presence of dialkylcyanamide in the cyanate ester during curing processes can cause out-gassing and deterioration of the cured product. Dialkylcyanamides are high boiling compounds, e.g., diethylcyanamide boils at 187° C., which remain in the cyanate ester during processing. They also are generally inert to curing reactions. When the cyanate ester is subjected to temperatures above the boiling point of the dialkylcyanamide either during curing reactions, post curing or in subsequent high temperature applications, the dialkylcyanamide will vaporize causing out-gassing and rupture of the thermoset structure. It is very important that the amount of dialkylcyanamide in the cyanate esters be kept to a minimum.

Commercially available polycyanate esters are either crystalline materials having crystalline melting points above 70° C., such as the cyanate ester described in U.S. Pat. No. 4,028,393, or amorphous materials having viscosities above about 100,000 cps at 25° C., such as the cyanate ester described in Example 9 of U.S. Pat. No. 4,748,270.

The crystalline dicyanate esters, e.g., the dicyanate ester of Bisphenol A, can be readily purified by one or more recrystallizations. Residual reactants, e.g., tertiary amines, and by-products, e.g., dialkylcyanamide, are readily removed by the recrystallization procedure.

Amorphous polycyanate esters which have viscosities above about 100,000 cps at 25° C., are relatively stable at room temperature even in the presence of tertiary amine impurities. It is a well known fact that materials in the solid or frozen state are storage stable and relatively inert. Furthermore, polycyanate esters, which have high cyanate equivalent weights are less reactive than cyanate esters having low equivalent weights. Being less reactive, such polycyanate esters can withstand processing to remove impurities, such as dialkylcyanamides, with a minimum of trimerization reaction.

Bis(4-cyanatophenyl)-1,1-ethane has a crystalline melting point below 30° C. and its usual physical state at room temperature is a low viscosity super-cooled liquid, the viscosity being less than 200 cps at 25° C. This ester being very mobile at room temperature and having a low cyanate equivalent weight (theoretical 132) is very sensitive to impurities, particularly tertiary amine impurities. When a tertiary amine, e.g., triethylamine, is present in the cyanate ester in amounts above about 50 ppm, the cyanate ester will increase in viscosity at the rate proportional to the concentration of tertiary amine and unreacted phenolic hydroxyl. For example, bis(4-cyanatophenyl)-1,1-ethane prepared by the general procedure described in U.S. 3,553,244 which contained 72 ppm triethylamine bodied to a hard resin after 7 days at 50° C. Before gelation occurs and when the viscosity approaches 250 cps, the ester becomes cloudy and separates into two phases. When the tertiary amine content is below about 50 ppm, bis (4-cyanatophenyl)-1,1-ethane is stable at room temperature having an increase in viscosity of less than 100 cps over 26 weeks and at elevated temperatures, e.g., 110° C., has a reactivity of less than 0.3 percent trimerization (consumption of cyanate groups) per hour.

When the by-product, dialkylcyanamide, is present in bis(4-cyanatophenyl)-1,1-ethane in quantities less than 1000 ppm, out-gassing and rupture of the resinous structures during and after cure are not problems.

The bis(4-cyanatophenyl)-1,1-ethane of this invention is made by reacting bis(4-hydroxyphenyl)-1,1-ethane with cyanogen chloride or bromide using a tertiary amine as acid acceptor and a halocarbon as solvent. The tertiary amines useful in this invention correspond to the formula

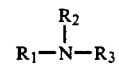

wherein $R_1$, $R_2$ and $R_3$ are the same or different and represent alkyl groups having from 1 to 18 carbon atoms, phenyl and substituted phenyl groups, cycloalkyl groups having 5 to 7 carbon atoms or cycloalkyl radicals having 6 carbon atoms interrupted by $C_1$ to $C_4$ alkylene groups. Examples of such amines are trimethylamine, triethylamine, methyldiethylamine, triisopropylamine, tributylamine methyldibutylamine, dimethylstearyl amine, dimethylcyclohexylamine, diethylaniline, and the like. A preferred amine is triethylamine.

The solvents used in this invention are halocarbon solvents, e.g., methylene dichloride, dichloroethane, perchloroethylene, chlorobenzene, dichlorobenzene and the like. The preferred solvent is methylene dichloride.

In carrying out the process of this invention, cyanogen chloride is dissolved in a halocarbon at a concentration of about 5 weight percent up to about 50 weight percent cyanogen chloride based on the weight of the solution. The solution is then cooled to about −10° C. to about −40° C., preferably about −20° C. to about −30° C. A solution of the dihydric phenol and the tertiary amine in a halocarbon solvent which is preferably prepared by adding slowly the tertiary amine to a slurry of the dihydric phenol in the halocarbon solvent, is then added to the cyanogen chloride solution at such a rate that the temperature stays within the range of about −10° C. to about −40° C., preferably about −20° C. to about −30° C. Generally, the addition will take about 30 minutes to about 3 hours depending upon the amount of reactants and the cooling capacity which is available. When the addition is completed, the solution is washed with acidified water to remove tertiary amine salts and any other water soluble by-products formed in the reaction. The washing is conducted by intimately mixing the acidified water and the halocarbon solution using a counter current extractor or other extraction means, allowing the phases to separate and drawing off the aqueous phase. Generally at least two acidified water washes are conducted. After the acidified water wash, washing can be conducted with water alone. The resulting washed halocarbon solution is then subjected to distillation to remove the halocarbon solvent. Batch distillation is conducted under such conditions that the temperature of the cyanate ester product does not exceed about 90° C. Higher temperatures, typically up to about 150° C. can be employed when distillation is accomplished in continuous thin-film evaporators.

The amount of halocarbon solvent which is used to dissolve the dihydric phenol and tertiary amine is that amount which is required to form a handleable solution. Generally, at least about 20 weight percent solvent, based on the weight of the solution, is needed. However, much higher amounts of solvent, up to about 75 weight percent, can be used. The upper limit on the amount used is based mainly upon economic considerations. Preferably, the amount of solvent will be about 15 to about 35 weight percent.

In preparing the composition of this invention, the reaction is conducted so that there is always a stoichiometric excess of cyanogen chloride to dihydric phenol. The ratio of the equivalents of cyanogen chloride to dihydric phenol will vary from about 1.05 to about 1.25.

The amount of tertiary amine which is used as the acid acceptor in the reaction of this invention will vary from about 1.005 to about 1.05 equivalents per each equivalent of the dihydric phenol.

In order to obtain substantially complete reaction of the phenolic hydroxyls with the cyanogen chloride, to reduce or eliminate the reaction of the cyanate group with the phenolic group, and to reduce or eliminate the reaction of cyanogen chloride with the tertiary amine, a solution of the dihydric phenol salted with the tertiary amine and containing a slight excess of tertiary amine is added to the solution of cyanogen chloride, and the reaction is conducted under such conditions that the temperature is kept under $-10°$ C. throughout the reaction.

The bis(4-cyanatophenyl)−1,1-ethane of this invention has a viscosity of less than 200 cps at 25° C., preferably about 75 to about 150 cps, a reactivity at 110° C. of less than 0.3 percent trimerization per hour, and contains less than 50 ppm of tertiary amine and less than 1000 ppm of dialkylcyanamide. The cyanate ester has a crystalline melting point of about 29° C. However, unless seeded with crystals, the cyanate ester remains in the liquid state. Even when crystallization occurs, the crystals are easily melted by gentle heating.

Reactivity of the dicyanate ester refers to the ability of the cyanate groups to cyclotrimerize. When cyclotrimerization occurs, cyanate ester content is reduced. The cyanate ester content can be determined quantitatively by infrared analysis or by "residual heat of reaction" using a differential scanning calorimeter.

Cyclotrimerization is accompanied by an increase in refractive index which is directly proportional to the conversion of cyanate groups to the triazine ring. A plot of the refractive index versus the percent conversion of cyanate functionality to s-triazine esters, as determined by infrared or differential scanning analysis, is linear and the slope constant is readily determined.

The reactivity of bis(4-hydroxyphenyl)-1,1-ethane is determined by measuring the change in refractive index at 110° C. and dividing this value by the previously determined slope constant. The composition of this invention has a reactivity of less than 0.3 percent trimerization per hour and, preferably, less 0.1 percent per hour.

The amounts of tertiary amine impurity and dialkylcyanamide impurity can be determined by gas chromatographic analysis. Using this procedure, a sample of the dicyanate ester product is introduced into a gas-liquid partition column, the compounds are separated as they pass through the column with the carrier gas, and their presence in the effluent is detected and recorded as a chromatogram. The component content is determined from the chromatogram by comparing the area of the component peak in the sample with an area of the same component in a known standard. The bis(4-cyanatophenyl)-1,1-ethane of this invention contains less than 50 ppm of tertiary amine, preferably less than 25 ppm, and less than 1000 ppm of dialkylcyanamide, preferably less than 500 ppm.

Bis(4-cyanatophenyl)-1,1-ethane of this invention can be blended with other cyanate esters to form low viscosity blends which either do not crystallize or crystallize at a slow rate. Such other cyanate esters are made from the reaction of cyanogen halide with polyhydric phenols, such as resorcinol, bis(4-hydroxyphenyl) methane, bis(4-hydroxyphenyl)-2,2-propane (or Bisphenol A as it is commonly called), bis(4-hydroxyphenyl)ether, bis(4- hydroxyphenyl)sulfide, bis(4-hydroxy-3,5- dimethylphenyl)methane, bis(4-hydroxy-3,5-dimethylphenyl)- 2,2-propane, bis(4-hydroxy-3,5-dimethylphenyl)ether, bis(4-hydroxy-3,5-dimethylphenyl) sulfide, 4,4'-(hexafluoroisopropylidene)diphenol, p,p',p''-(trihydroxytriphenyl)ethane, dihydroxy-naphthalene, novolak resins and the like.

Any amount of the dicyanate ester of this invention can be blended with the other cyanate esters, e.g., 99 to 1 parts by weight to 1 to 99 parts by weight. Preferred blends are about 70 to about 95 parts by weight of the dicyanate ester of this invention with about 30 to about 5 parts by weight, the total being 100 parts, of the dicyanate esters of bis(4-hydroxyphenyl)-2,2-propane or bis(4-hydroxy-3,5-dimethyl- phenyl) methane.

A particularly important aspect of this invention is the use of the dicyanate ester of this invention to form blends with prepolymers of dicyanate esters.

Prepolymers are generally amorphous in form and possess an oligomeric physical state which is more suited for use in prepregging operations than the crystalline or semi-crystalline unpolymerized cyanate esters. Prepolymers are made by heating the dicyanate ester with or without catalyst at a temperature of about 140° C. to about 240° C. for a time sufficient to cyclotrimerize from about 5 to about 50 percent of the cyanate functional groups and, preferably, about 15 to about 40 percent of the cyanate functional groups. Useful prepolymers possess melt viscosities ranging from about 1,000 cps. at 50° C. up to 1,000,000 cps. Catalysts which can be used in preparing the prepolymers are mineral or Lewis acids, bases such as alkali metal hydroxides, alkali metal alcoholates or tertiary amines, salts such as sodium carbonate or lithium chloride, or active hydrogen containing compounds, such as bisphenols and monophenols. It is preferred to conduct the prepolymerization reaction without a catalyst, utilizing only heat followed by thermal quenching, in the manner taught by British Patent No. 1,305,762 which is hereby incorporated by reference.

Prepolymer formation is determined by measuring the percent trimerization using the procedure described for determining percent reactivity.

Prepolymers can be made by homopolymerizing or copolymerizing the dicyanate esters described hereinbefore. Particularly preferred prepolymers are made by homopolymerizing the dicyanate ester of bis(4-hydroxyphenyl)-2,2-propane or bis(4-hydroxy-3,5-dimethylphenyl)methane, or by copolymerizing these dicyanate esters as described in commonly assigned application, Ser. No. 904,610, filed Sept. 8, 1986.

Blended compositions can be made with any amount of low viscosity dicyanate ester and prepolymer, e.g., 99 to 1 parts by weight of monomeric dicyanate ester to 1 to 99 parts by weight of prepolymer. Useful blends are made from about 5 to about 80 parts by weight of low viscosity dicyanate ester to about 95 to about 20 parts by weight of prepolymer.

The dicyanate ester-prepolymer blends are particularly useful in hot melt prepregging for aircraft structural composites and film adhesives. Hot melt prepregs are made by melting the prepolymer blends and applying them as films to release paper. Unidirectional carbon fibers are laid down on the hot sticky film and another release paper is placed on top of the film and fibers. Resin impregnation of the fiber is achieved by hot-rolling the "sandwich". The prepreg is then stored under refrigeration. For use, the prepreg is thawed at room temperature, cut into required shapes, stripped of protective release paper and laid-up on molds for vacuum-bag curing. For large structural composites, e.g. tail structure of aircraft, up to a week may be needed to complete the lay-up. If the prepregs crystallize during this time, they will become stiff and boardy and will be difficult to conform to the desired shape. At least one week of freedom from crystallization at room temperature to 120° F., the temperature range in which prepregs are usually applied to the mold, is desired by structural composite manufacturers.

The prepolymer blends are non-crystallizing liquids and semisolids which are appreciably lower in viscosity at process temperatures in the range of 20° C. to 140° C. than are the unblended prepolymers.

The composition of this invention in either unblended or blended form can be cured by heat alone but is preferably cured by the use of a catalyst plus heat. Such curing catalysts include those described above which are used in preparing prepolymers. Additional catalysts are those described in U.S. Pat. Nos. 3,962,184, 3,694,410 and 4,026,213 which are hereby incorporated by reference. Examples of such catalysts include zinc octoate, tin octoate, zinc stearate, tin stearate, copper acetylacetonate, phenol, catechol, triethylenediamine and chelates of iron, cobalt, zinc, copper, manganese and titanium with bidentate ligands such as catechol. Such catalysts are used in the amounts of about 0.001 to about 20 parts by weight per 100 parts by weight of the cyanate ester blend. A preferred catalyst system is that described in U.S. Pat. No. 4,604,452. Such catalysts are liquid solutions of a metal carboxylate and an alkylphenol, e.g., zinc naphthenate and nonylphenol. These catalyst are used in the amounts of about 0.001 to about 0.5 part by weight of metal and about 1 to about 20 parts by weight of alkylphenol per 100 parts by weight of cyanate ester blend.

The composition of this invention is cured by heating at elevated temperatures for a time sufficient to obtain a complete cure, i.e., until at least about 80 percent of the cyanate functional groups are cyclotrimerized. The curing reaction can be conducted at one temperature or can be conducted by heating in steps. If conducted at one temperature, the temperature will vary from about 250° F. to about 450° F. When conducted by stepwise heating, the first step, or gelation step, is performed at a temperature of about 150° F. to about 350° F. The curing step is conducted at a temperature of about 300° F. to about 450° F., and the optional post-curing step is conducted at a temperature of about 400° F. to about 550° F. The overall curing reaction will take about 5 minutes to about 8 hours.

The dicyanate ester blends and co-prepolymers can be blended with polyepoxide resins and can be cured to form useful thermoset compositions. Up to about 70 weight percent based on total blend weight can be polyepoxide resin. Such polyepoxide resins are the well-known glycidyl ethers of polyhydric phenols which are made by reacting an epihalohydrin, preferably epichlorohydrin, with a polyhydric phenol, preferably Bisphenol A.

The composition of this invention is particularly useful when blended with various thermoplastic resins, particularly amorphous aromatic thermoplastic resins.

When formulating for particular end uses, additional components can be incorporated in the polycyanate composition. Such components include minor amounts of reinforcing fibers, colloidal silica flow modifiers, mineral fillers and pigments.

The cured compositions of this invention can be used in vacuum bagged structural composites, transfer molded encapsulates, filmed structural adhesives, printed wiring boards and composites for aircraft primary structures.

The following examples will describe the invention in more detail. Parts and percentages unless otherwise indicated are parts and percentages by weight. BADCy referred to in the examples is bis(4-cyanatophenyl)-2,2-propane. METHYLCy is bis(4-cyanato-3,5-dimethylphenyl)methane. BEDCy is bis(4-cyanatophenyl)-1,1-ethane. FLUOROCy is the dicyanate ester of 4,4'-hexafluoroisopropylidene diphenol. ER509 is the diglycidyl ether of Bisphenol A having an epoxide equivalent weight of 185. ER 5163 is the diglycidyl ether of tetrabromobisphenol A having an epoxide equivalent weight of 400.

EXAMPLE 1

To a suitable reactor were added 1050 parts of methylene chloride. The temperature was lowered to 2° C. and cyanogen chloride was introduced into the reactor as a sparge below the surface of the methylene chloride. 258.9 parts of cyanogen chloride were added over a period of 70 minutes with the temperature rising to 13° C. A solution of 409.5 parts of bis(4-hydroxyphenyl)-1,1-ethane, 391.1 parts of triethylamine and 574.1 parts of methylene chloride was added to an addition funnel. The reactor contents were cooled to −30° C., and addition of the solution from the funnel was begun. The addition was completed in 53 minutes with the temperature being held at −30° C. The reactor contents were then washed with a solution of 11.1 parts of aqueous 37 percent hydrochloric acid in about 2 liters of water by vigorous agitation for 5–10 minutes. Agitation was stopped and the aqueous layer was drawn off. Washing with acidified water—7.4 parts of 37 percent HCl in 2 liters of water—was repeated and was followed by two washes with deionized water. The dicyanate ester product, 500.0 parts, was recovered by removing the methylene chloride solvent by distillation under vacuum to a pot temperature of 70° C.

The resulting product, bis(4-cyanatophenyl)−1,1-ethane) (BEDCy), had a viscosity of 81 cps at 25° C. After 10 days at 50° C., the viscosity, measured at 25° C., was 84 cps. The reactivity at 110° C. as measured by refractive index was 0.26 percent per hour. The product contained 1 ppm of triethylamine and 518 ppm of diethylcyanamide.

COMPARATIVE EXAMPLE

Bis(4-cyanatophenyl)-1,1-ethane was made by adding triethylamine, in an amount equivalent to the diphenol, to a solution of the diphenol and cyanogen chloride by the following procedure.

To 525 parts methylene chloride in a suitable reactor were added 96 parts of cyanogen chloride as a sparge below the surface of the methylene chloride. The addition was completed in 44 minutes with the temperature rising from 2° C. to 9° C. The temperature was lowered to 0° C. and a solution of 151.8 parts of bis(4-hydroxyphenyl)-1,1-ethane in 189.2 parts of acetone was added in 7 minutes while the temperature was lowered to −10° C. Triethylamine, 143.6 parts, was added over 19 minutes while keeping the temperature at −10° C. The reactor contents were then washed with 1 liter of water by vigorous agitation for 5-10 minutes. The agitation was stopped and the aqueous layer was drawn off. The washing was repeated 3 times. The dicyanate ester product, 182.6 parts, was recovered by removing the solvent by vacuum distillation to a pot temperature of 70° C.

The resulting product had a viscosity of 115 cps at 25° C. After 10 days at 50° C., the product had polymerized to a solid with a portion being a cloudy separated prepolymer. The product contained 72 ppm of triethylamine and 4549 ppm diethylcyanamide. The reactivity at 110° C. as measured by refractive index was 8.37 percent per hour.

EXAMPLE 2

Catalysts, nonylphenol (NP), copper naphthenate, 8 percent Cu (CuN) and/or zinc naphthenate, 8 percent Zn(ZnN) were dissolved in the cyanate ester of Example 1 (BEDCy). The time to gel at 220° F. was determined. The curable compositions were poured into aluminum moldes heated according to the following cure schedules:

| Schedule | a | b | c | d |
|---|---|---|---|---|
| Hours @350° F. | 1 | 3 | 3 | 2 |
| Hours @410° F. | 1 | 0 | 1 | 2 |
| Hours @482° F. | 2 | 0 | 1 | 0 |

The physical properties of the cured casting were then predetermined. The details of the formulations and the test results are shown in Table 1.

TABLE 1

| | Properties of Thermoset BEDCy | | | |
|---|---|---|---|---|
| Example | 2A | 2B | 2C | 2D |
| BEDCy | 160 | 160 | 160 | 160 |
| NP | 3.2 | 9.6 | 9.6 | 3.2 |
| CuN | 0.3 | 0.4 | 0.4 | |
| ZnN | | | | 0.24 |
| Gel Temp °F. | 220 | 220 | 220 | 220 |
| Minutes to Gel | 200 | 55 | 55 | 15 |
| Cure Schedule | (a) | (b) | (c) | (d) |
| Cured Properties | | | | |
| HDT °C. | | | | |
| Dry | 226 | 186 | 214 | 249 |
| After 64 hr H$_2$O Boil | 143 | 143 | 148 | 183 |
| After 208 hr H$_2$O Boil | 135 | 138 | 145 | 174 |
| Flexure | | | | |
| Strength, KSI | 22.4 | 27.2 | 24.8 | 23.5 |
| Modulus, MSI | 0.39 | 0.44 | 0.42 | 0.40 |
| Strain % | 6.9 | 8.1 | 7.8 | 7.7 |
| MeCl$_2$ Absorp. wt % | | | | |
| 1 hr @25° C. | +1.7 | +5.4 | +1.5 | +2.74 |
| 3 hr @25° C. | 3.9 | 14.2 | 5.9 | 4.95 |
| 6 hr @25° C. | 5.65 | 20.6 | 9.4 | 7.0 |

TABLE 1-continued

| | Properties of Thermoset BEDCy | | | |
|---|---|---|---|---|
| Example | 2A | 2B | 2C | 2D |
| H$_2$O Absorb wt % | | | | |
| 24 hrs @100° C. | 1.44 | 1.05 | 1.15 | 1.39 |
| 48 hrs @100° C. | 1.75 | 1.35 | 1.39 | 1.59 |
| 208 hrs @100° C. | 2.08 | 1.65 | 1.58 | 1.80 |
| Flammability, UL 94 | | | | |
| Seconds to Extinguish | | | | |
| 1st Burn | — | — | — | 1 |
| 2nd Burn | — | — | — | Consumed |
| Dk @1 MHz | | | | |
| Dry | 2.99 | | | 2.98 |
| After 48 hrs H$_2$O Boil | 3.39 | | | 3.37 |
| Df @1 MHz | | | | |
| Dry 10$^{-3}$ | 4.9 | | | 4.9 |
| After 48 hrs H$_2$O Boil 10$^{-2}$ | 1.7 | | | 1.4 |

EXAMPLE 3

The cyanate ester prepared as Example 1, BEDCy, was blended with MethylCy, BADCy and FLUOROCy and the blends were cured using the procedure of Example 2. The details of the blends and the physical properties of the cured blends are shown in Table II.

TABLE II

| | Properties of Cyanate Ester Blends | | | |
|---|---|---|---|---|
| Example | 3A | 3B | 3C | 3D |
| BEDCy | 40 | 80 | 80 | 80 |
| METHYLCy | 120 | 80 | | |
| BADCy | | | 80 | |
| FLUOROCy | | | | 80 |
| NP | 3.2 | 3.2 | 3.2 | 3.2 |
| ZnN | 0.24 | 0.24 | 0.24 | 0.24 |
| Gel Temp °F. | 250 | 250 | 250 | 250 |
| Minutes to Gel | 205 | 230 | 5 | 2 |
| Cure Schedule | (a) | (a) | (a) | (a) |
| Cured Properties | | | | |
| HDT °C. | | | | |
| Dry | 247 | 241 | 246 | 220 |
| After 64 hr H$_2$O Boil | 207 | 198 | 156 | 167 |
| After 208 hr H$_2$O Boil | 202 | 190 | 150 | 165 |
| Flexure | | | | |
| Strength, KSI | 17.3 | 20.3 | 22.8 | 22.1 |
| Modulus, MSI | 0.42 | 0.44 | 0.40 | 0.43 |
| Strain, % | 4.3 | 5.0 | 6.9 | 5.6 |
| MeCl$_2$ Absorb. Wt % | | | | |
| 1 hr @25° C. | +4.05 | +3.75 | +2.4 | +3.15 |
| 3 hr @25° C. | 8.15 | 6.96 | 5.1 | 7.7 |
| 6 hr @25° C. | 12.0 | 10.1 | 7.6 | 12.3 |
| H$_2$O Absorb. Wt % | | | | |
| 24 hrs @100° C. | 1.72 | 1.47 | 1.49 | 0.99 |
| 48 hrs @100° C. | 1.71 | 1.58 | 1.78 | 1.16 |
| 208 hrs @100° C. | 1.84 | 1.73 | 2.03 | 1.38 |
| Flammability UL 94 | | | | |
| Seconds to Extinguish | | | | |
| 1st Burn | 1 | 0 | 0 | 0 |
| 2nd Burn | 6 | 15 | 17 | 0 |
| Dk @1 MHz | | | | |
| Dry | 2.86 | 2.91 | 2.96 | 2.92 |
| After 48 hr H$_2$O Boil | 3.26 | 3.31 | 3.36 | 3.18 |
| Df @1 MKz | | | | |
| Dry × 10$^{-3}$ | 5.2 | 6.1 | 5.0 | 5.0 |
| After 48 hr H$_2$O Boil × 10$^{-2}$ | 1.2 | 1.3 | 1.5 | 1.3 |

EXAMPLE 4

Blends were made with the cyanate ester of Example 1, BEDCy, the diglycidyl ether of Bisphenol A, ER509, and the diglycidyl ether of tetrabromo bisphenol A, ER5163. These blends were cured using the procedure described in Example 2. Details of the blends and their cured properties are listed in Table III. In addition to nonyl phenol (NP), copper acetylacetonate, 24.3 % Cu (CuAcAc) was used as catalyst.

TABLE III

Blends of BEDCy and Epoxy Resins

| Example | 4A | 4B |
|---|---|---|
| BEDCy | 56 | 120 |
| ER509 | 104 | |
| ER5163 | | 40 |
| NP | 3.2 | 3.2 |
| CuAcAc | 0.08 | 0.08 |
| Gel Temp °F. | 250 | 250 |
| Minutes to Gel | 165 | 135 |
| Cure Schedule | (d) | (d) |
| Cured Properties | | |
| HDT °C. | | |
| Dry | 214 | 205 |
| After 64 hr H$_2$O Boil | 160 | 154 |
| After 208 hr H$_2$O Boil | 157 | 146 |
| Flexure | | |
| Strength, KSI | 11.7 | 24.8 |
| Modulus, MSI | 0.4 | 0.44 |
| Strain, % | 3.1 | 6.9 |
| MeCl$_2$ Absorb. Wt % | | |
| 1 hr @25° C. | +0.81 | +1.86 |
| 3 hr @25° C. | 1.60 | 4.3 |
| 6 hr @25° C. | 2.23 | 7.35 |
| H$_2$O Absorb. Wt % | | |
| 24 hrs @100° C. | 1.09 | 1.07 |
| 48 hrs @100° C. | 1.23 | 1.35 |
| 208 hrs @100° C. | 1.33 | 1.65 |
| Flammability UL94 | | |
| Seconds to Extinguish | | |
| 1st Burn | 35 | 0 |
| 2nd Burn | 3 | 0 |
| Dk @1 MHz | | |
| Dry | 3.18 | 3.06 |
| After 48 hr H$_2$O Boil | 3.53 | 3.37 |
| Df @1 MHz | | |
| Dry × 10$^{-3}$ | 1.18 | 5.5 |
| After 48 hr H$_2$O Boil × 10$^{-2}$ | 2.2 | 1.5 |

EXAMPLE 5

A prepolymer (Prepolymer 1) was prepared by reacting 50 parts of METHYLCy with 50 parts of BADCy at 210° C. until the refractive index at 110° C. was 1.5427, indicating 21 percent trimerization. The prepolymer had a viscosity of 55,200 cps at 77° F.

Another prepolymer (Prepolymer 2) was prepared by reacting 100 parts of BADCy at 190° C. until the refractive index at 110° C. was 1.5622, indicating 31.5 percent trimerization. The viscosity of Prepolymer 2 was 5,200,000 cps at 77° F.

Prepolymer 1 and Prepolymer 2 were blended with various amounts of BEDCy and the viscosity of the blends at 25° C. was determined. The blends were then poured into Gardner-Holdt viscosity tubes, the tubes were sealed and placed in a hot box at 50° C. The viscosity of the blends after aging at 50° C. was determined over a period of time. The crystallization development at room temperature and at 50° C. was also determined.

Prepolymer 1 and Prepolymer 2 were also blended with BADCy monomer. The blends crystallized before viscosities could be determined.

The viscosities (measured at 25° C.) and crystallization tendencies are listed in Table IV:

TABLE IV

| Components | A | B | C | D | E | F |
|---|---|---|---|---|---|---|
| BEDCy | 6.0 | 10.0 | 14.0 | 12.0 | 8.0 | 15.0 |
| PREPOLYMER 1 | 14.0 | 10.0 | 6.0 | — | — | — |
| PREPOLYMER 2 | — | — | — | 8.0 | 12.0 | 5.0 |
| Init. Visc. (cps) | 10,900 | 1860 | 500 | 1560 | 9750 | 475 |
| 1 wk at 50° C. | Z$_6$+ | Z$_1$ | T-U | Z | Z$_6$ | U |
| 1 wk at R.T. | | | No crystals | | | |
| 2 wk at 50° C. | Z$_6$-Z$_7$ | Z$_1$-Z$_2$ | U-V | Z$_1$+ | Z$_6$-Z$_7$ | U-V |
| 2 wk at R.T. | | | No crystals | | | |

EXAMPLE 6

BEDCy was blended with Prepolymer 1 and Prepolymer 2 described in Example 5. The blends were poured into molds and cured, and the physical properties were determined using the procedure described in Example 2.

BEDCy was also blended with BADCy, METHYLCy and the diglycidyl ether of Bisphenol A having an epoxide equivalent weight of 185. Castings were also prepared from this blend and the physical properties were determined.

The physical properties of the castings are listed in Table V.

TABLE V

| Components | A | B | C |
|---|---|---|---|
| BEDCy | 60 | 50 | 70 |
| PREPOLYMER 1 | | 50 | |
| PREPOLYMER 2 | 40 | | |
| BADCy | | | 15 |
| METHYLCy | | | 15 |
| ER509 | | | 15 |
| NP | 2.0 | 2.0 | 4.0 |
| CuN | | | 0.31 |
| ZnN | 0.15 | 0.15 | |
| Gel Temp °F. | 220 | 220 | 220 |
| Minutes to Gel | 90 | 85 | 20 |
| Cure Schedule | (a) | (a) | (a) |
| HDT (°C.) | | | |
| Dry | 195 | 202 | 178 |
| Wet* | 159 | 176 | 145 |
| % H$_2$O Abs.* | 1.62 | 1.64 | 1.46 |
| Flexure Strength (psi) Dry @R.T. | 25,200 | 22,800 | 27,200 |
| Flexure Modulus (10$^6$ psi) Dry @R.T. | 0.44 | 0.43 | 0.46 |
| Flexure Strain (%) Dry @R.T. | 8.05 | 6.36 | 8.94 |
| Flexure Strength (psi) Wet at 180° F.** | 14,900 | 16,500 | 13,400 |
| Flexure Modulus (10$^6$ psi) Wet at 180° F.** | 0.40 | 0.39 | |
| Flexure Strain (%) Wet at 180° F.** | >12.0 | 11.55 | >12.00 |

*Test bars conditioned 64 hours at 200° F. and >95 percent R.H.
**Flexure bars conditioned 48 hours in boiling water prior to testing The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing bis(4-cyanatophenyl)-1,1-ethane having a viscosity of less than 200 cps at 25° C., a reactivity at 110° C. of less than 0.3 percent trimerization per hour, and containing impurities of less than 50 ppm of tertiary amine and less than 1000 ppm of diethylcyanamide which comprises:
- a) reacting a solution of cyanogen halide selected from cyanogen chloride or bromide in a halocarbon solvent with a solution of bis(4-hydroxyphenyl)-1,1-ethane, and a tertiary amine in a halocarbon solvent at a temperature below about −10° C. for a time sufficient to complete the esterification reaction;
- b) washing the resulting solution with aqueous acid, and
- c) recovering the cyanate ester product, wherein the cyanogen chloride and the dihydric phenol are present in the amount of about 1.05 to about 1.25 equivalents of cyanogen chloride to one equivalent of dihydric phenol and wherein the tertiary amine is present in the amount of about 1.005 to about 1.05 equivalents per each equivalent of the dihydric phenol.

2. The process of claim 1 wherein the temperature is between about −10° C. and about −40° C.

3. The process of claim 2 wherein the temperature is between about −20° C. and about −30° C.

4. The process of claim 1 wherein the tertiary amine is triethylamine.

5. The process of claim 1 wherein the halocarbon solvent is methylene chloride.

6. The process of claim 1 wherein the cyanogen halide is cyanogen chloride.

7. The process of claim 1 wherein the tertiary amine is added to a slurry of the dihydric phenol in the halocarbon solvent to form a solution.

* * * * *